United States Patent
Lee

(10) Patent No.: US 10,314,539 B2
(45) Date of Patent: Jun. 11, 2019

(54) APPARATUS AND METHOD FOR MEASURING BIOLOGICAL SIGNAL

(71) Applicant: SAMSUNG ELECTRONICS CO., LTD., Suwon-si (KR)

(72) Inventor: Juneyoung Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 274 days.

(21) Appl. No.: 14/802,464

(22) Filed: Jul. 17, 2015

(65) Prior Publication Data

US 2016/0192885 A1 Jul. 7, 2016

(30) Foreign Application Priority Data

Jan. 7, 2015 (KR) .................. 10-2015-0002025

(51) Int. Cl.
*A61B 5/00* (2006.01)
*A61B 5/053* (2006.01)

(52) U.S. Cl.
CPC .......... *A61B 5/6841* (2013.01); *A61B 5/0059* (2013.01); *A61B 5/053* (2013.01); *A61B 5/489* (2013.01)

(58) Field of Classification Search
CPC ... A61B 5/6841; A61B 5/6842; A61B 5/0059; A61B 5/1455
See application file for complete search history.

(56) References Cited

U.S. PATENT DOCUMENTS

| 6,016,435 A * | 1/2000 | Maruo ............... A61B 5/14532 600/316 |
| 6,631,282 B2 * | 10/2003 | Rule .................. A61B 5/14532 600/344 |
| 7,146,221 B2 * | 12/2006 | Krulevitch ........... A61N 1/0543 607/116 |
| 2010/0204588 A1 | 8/2010 | Kim et al. |
| 2014/0276113 A1 * | 9/2014 | Chiu .................... A61B 5/6842 600/479 |
| 2015/0018642 A1 * | 1/2015 | Gulati ................. A61B 5/1455 600/316 |

FOREIGN PATENT DOCUMENTS

| JP | 2000-41204 A | 2/2000 |
| JP | 3174783 U | 3/2012 |
| KR | 10-2010-0091836 A | 8/2010 |
| KR | 10-2011-0095027 A | 8/2011 |
| KR | 10-2011-0105363 A | 9/2011 |
| KR | 10-2013-0016835 A | 2/2013 |
| KR | 10-1310405 B1 | 9/2013 |
| KR | 10-2014-0033782 A | 3/2014 |

* cited by examiner

*Primary Examiner* — William J Levicky
(74) *Attorney, Agent, or Firm* — Sughrue Mion, PLLC

(57) ABSTRACT

Provided are apparatuses for and methods of measuring a biological signal. The biological signal measuring apparatus includes reference point sensors configured to detect signals detected from at least two reference marks on a surface of a subject and a biological signal measuring position detector configured to generate information about a biological signal measuring position based on the signals detected from the at least two reference marks. The biological signal measuring apparatus measures the biological signal according to the information about the biological signal measuring position.

14 Claims, 11 Drawing Sheets

APPARATUS AND METHOD FOR MEASURING BIOLOGICAL SIGNAL

CROSS-REFERENCE TO RELATED APPLICATION

This application claims priority from Korean Patent Application No. 10-2015-0002025, filed on Jan. 7, 2015 in the Korean Intellectual Property Office, the disclosures of which is incorporated herein in its entirety by reference.

BACKGROUND

1. Field

Apparatuses and methods consistent with exemplary embodiments relate to measuring a biological signal, whereby a measuring position of a biological signal may be detected.

2. Description of the Related Art

Along with the advances in medical science and the increase of the average life expectancy, the interest in health care and related medical devices has also increased. In addition, the interest in small-and medium-sized medical devices used in public places and small medical devices and health care devices used at home or carried by individuals as well as over various medical devices used in hospitals or health examination centers has increased.

Since biological signals detected from a living organism vary with the respective organs, the biological signals should be continuously measured at a fixed position in order to accurately sense a change of the living organism by measuring the biological signals. However, when a medical device is installed in a wearable apparatus, the biological signal measuring position may change due to a movement of the living organism. As a result, the reliability of measured biological signal data may decrease.

SUMMARY

One or more exemplary embodiments provide apparatuses for and methods of measuring a biological signal capable of improving a reliability of measured biological signal data by uniformly maintaining a measuring position of a biological signal.

According to an aspect of an exemplary embodiment, there is provided a biological signal measuring apparatus includes a plurality of reference point sensors configured to detect signals detected from at least two reference marks on a surface of a subject; a biological signal measuring position detector configured to generate information about a biological signal measuring position based on the signals detected from the at least two reference marks; and a biological signal measuring sensor configured to measure the biological signal according to the information about the biological signal measuring position.

The biological signal measuring position detector may be further configured to store information about reference signals detected from the at least two reference marks.

The biological signal measuring position detector may be further configured to compare the signals detected from the reference marks with the reference signals to generate the information about the biological signal measuring point.

The biological signal measuring position detector may be further configured to determine whether a degree of similarity between the signals detected from the reference marks and the reference signals is within an allowable range.

The biological signal measuring sensor may be further configured to measure the biological signal only when the biological signal measuring position detector determines that the degree of similarity is within the allowable range.

The biological signal measuring sensor may determine and store the measured biological signal as a valid signal only when the biological signal measuring position detector determines that the degree of similarity is within the allowable range.

Each of the plurality of reference point sensors may include a light source to radiate a light onto the surface of the subject on which the reference marks are attached and a spectrum analyzer to analyze a spectrum of the light reflected from the surface of the subject.

Each of the plurality of reference point sensors may include at least two electrodes that are in contact with the surface of the subject on which the reference marks are attached and an impedance measurer to measure an impedance between the at least two electrodes.

The biological signal measuring sensor may include a light source to radiate a light onto the biological signal measuring position and a spectrum analyzer to analyze a spectrum of the light reflected from the biological signal measuring position.

The biological signal measuring sensor may include at least two electrodes placed at the biological signal measuring position and an impedance measurer to measure an impedance between the at least two electrodes.

The reference marks may include at least one of polydimethylsiloxane (PDMS) and epoxy resin.

The biological signal measuring apparatus may include at least one of a tattoo sticker, an adhesive tape, or an E-skin on which the at least two reference marks are attached.

The biological signal measuring apparatus may include an alarm signal generator to generate an alarm signal if the biological signal measuring position detector determines that the degree of similarity is beyond the allowable range.

According to an aspect of another exemplary embodiment, there is provided a biological signal measuring method includes detecting signals generated from at least two reference marks on a surface of a subject; generating information about a biological signal measuring position based on the detected signals; and measuring a biological signal according to the information about the biological signal measuring position.

The generating the information about the biological signal measuring position may include storing information about reference signals corresponding to the at least two reference marks, and determining whether a degree of similarity between the detected signals and the reference signals is within an allowable range.

The measuring the biological signal may measure the biological signal only when the degree of similarity between the detected signals and the reference signals is within the allowable range.

The measuring the biological signal may include determining and storing the measured biological signal as a valid signal only when the degree of similarity between the detected signals and the reference signals is within the allowable range.

The biological signal measuring method may include generating of an alarm signal when the ratio of the signals detected from the reference marks and the reference signals is not within an allowable range.

The biological signal measuring method may further include displaying the at least two reference marks on a surface of the subject by using at least one from among a tattoo sticker, an adhesive tape, or an E-skin on which the at least two reference marks are attached.

According to an aspect of another exemplary embodiment, there is provided a biological signal measuring apparatus includes a storage configured to store a reference blood vessel image photographed at a reference point on a subject; a blood vessel photographing unit to photograph a blood vessel image of the subject; a biological signal measuring position detector to compare the photographed blood vessel image with the reference blood vessel image and generate information about a biological signal measuring position based on a result of the comparison; and a biological signal measuring sensor to measure a biological signal based on the information about the biological signal measuring position.

The blood vessel photographing unit may include a light source to radiate a light onto a surface of the subject, a measurer to measure a light absorption rate with respect to the subject, and an image generator to generate the photographed blood vessel image based on the light absorption rate.

The biological signal measuring position detector may determine whether a similarity of the blood vessel image photographed by the blood vessel photographing unit and the reference blood vessel image is within an allowable range.

The biological signal measuring apparatus may include an alarm signal generator configured to generate an alarm signal if the biological signal measuring position detector determines that the similarity between the photographed blood vessel image photographed and the reference blood vessel image is beyond the allowable range.

According to an aspect of another exemplary embodiment, there is provided a biological signal measuring method may include storing of a reference blood vessel image photographed at a reference point on a subject; photographing of a blood vessel image of the subject; comparing of the blood vessel image photographed by the blood vessel photographing unit with the reference blood vessel image and outputting information about a biological signal measuring position; and measuring of a biological signal based on the information about the biological signal measuring position.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
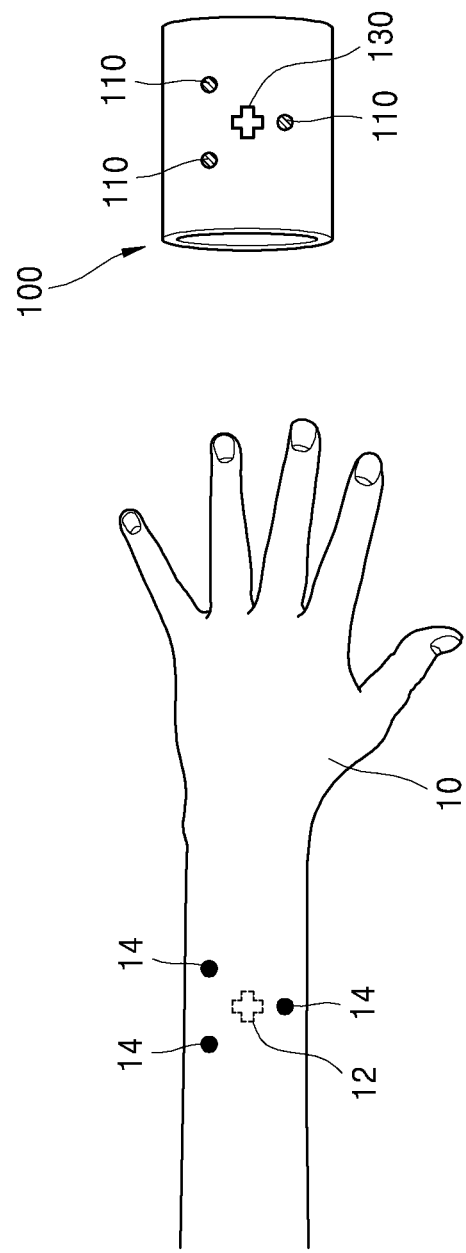
FIG. 1 is a view illustrating a biological signal measuring apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of", when preceding a list of elements, modify the entire list of elements and thus do not modify the individual elements of the list.

In the following description, when a layer, region, or component is referred to as being "above" or "on" another layer, region, or component, it can be directly or indirectly on the other layer, region, or component.

In the following embodiments, terms such as "first", "second", and so forth are used only for distinguishing one component from another component, rather than for restrictive meanings.

An expression used in the singular encompasses the expression of the plural, unless it has a clearly different meaning in the context. Also, throughout the specification, when a portion "includes" an element, another element may be further included, rather than excluding the existence of the other element, unless otherwise described.

Additionally, terms used herein, such as "unit" or "module", mean entities for processing at least one function or operation. These entities may be implemented by hardware, software, or a combination of hardware and software.

Figure 2:
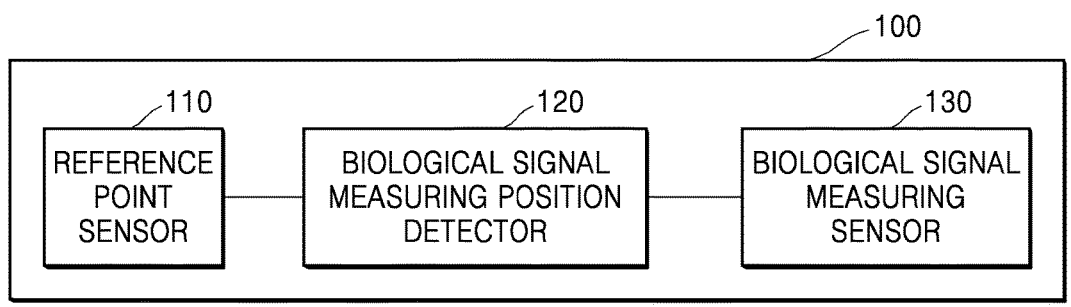
FIG. 2 is a block diagram of the biological signal measuring apparatus according to the exemplary embodiment of FIG. 1.

FIG. 1 is a view illustrating a biological signal measuring apparatus 100 according to an exemplary embodiment. FIG. 2 is a block diagram of the biological signal measuring apparatus according to the exemplary embodiment of FIG. 1.

The biological signal measuring apparatus 100 of FIG. 1 may be placed on a surface of a subject 10 to measure a biological signal from the subject 10. The biological signal may be a signal generated from the surface of the subject 10 and may include a reflected light signal or an electrical signal returning from the subject 10 after the light signal or the electrical signal is projected or applied onto the surface of the subject 10. Furthermore, the biological signal may include impedance information measured between any two points on the surface of the subject 10. The presented examples are not limited and the biological signal may be any signal having biological information of the subject 10. The biological information is subject-specific information and may be a signal according to a movement of a specific individual (e.g., heart or muscle) of the subject, such as electrocardiogram (ECG), ballistocardiogram (BCG), photoplethysmograph (PPG), electromyogram, and blood pressure, or may be information about material included in the subject, i.e., blood sugar, cholesterol, or the amount of body fat but is not limited thereto. The biological signal measuring apparatus 100 of FIG. 1 is a bracelet-type, but is not limited thereto. The biological signal measuring apparatus 100 according to an exemplary embodiment may be of any type that covers or is placed on the subject 10. Moreover, the biological signal measuring apparatus 100 according to another exemplary embodiment may be of a portable type that temporarily measures the biological signal from the surface of the subject 10 without covering or being placed on the subject 10.

Referring to FIGS. 1 and 2, the biological signal measuring apparatus 100 according to an exemplary embodiment may include reference point sensors 110 to detect signals detected from at least two reference marks 14 attached on the surface of the subject 10. Furthermore, the biological signal measuring apparatus 100 according to an exemplary embodiment may include a biological signal measuring position detector 120 to output information about a biological signal measuring position based on the signals detected from the at least two reference marks 14, and a biological signal measuring sensor 130 to measure the biological signal according to the information about the biological signal measuring position.

The reference marks 14 may be attached on the surface of the subject 10. Positions of the reference marks 14 on the subject 10 may be changed according to a target measuring position 12 where the biological information is measured. For example, positions of the reference marks 14 may be differently set in consideration of arrangement relationship between the reference point sensors 110 and 130 of the biological information measuring apparatus 100 and the target measuring position 12. Thus, the reference marks 14 may show a reference so as to match the biological signal measuring position with the target measuring position 12. The biological signal measuring position is a position at which the biological signal measuring sensor 130 measures the biological signal measuring position and, for example, may be a position of the subject 10 opposed to the biological signal measuring sensor 130. At least two reference marks 14 may be formed. When the reference point sensors 110 are located to correspond to the reference marks 14, the biological signal measuring position may be matched with the target measuring position 12.

The reference marks 14 may be attached on the surface of the subject 10 by using at least one of a tattoo sticker, an adhesive tape, or an E-skin. The tattoo sticker, the adhesive tape and the E-skin may have preliminary reference marks. The preliminary reference marks, as the reference marks 14, may be attached on the surface of the subject 10 when the tattoo sticker, the adhesive tape, or the E-skin is attached to the subject 10 and then is separated therefrom. The tattoo sticker, the adhesive tape, or the E-skin having the preliminary reference marks may form pairs with the reference point sensors 110. Therefore, the position of the preliminary reference marks on the tattoo sticker, the adhesive tape, or the E-skin and those of the reference point sensors 110 in the biological signal measuring apparatus 100 may correspond to each other.

The reference marks 14 may generate signals different from those generated from the surface of the subject 10 where the reference marks 14 are not attached. To achieve this, the reference marks 14 may independently generate the light signal or the electrical signal as described above. As another example, the reference marks 14 may have constituents different from that of the surface of the subject 10. The reference marks 14 may include at least one of polydimethylsiloxane (PDMS) and epoxy resin but is not limited thereto. By forming the reference marks 14 as described above, the signals detected from the reference marks 14 may be differentiated from that from another portion of the subject 10 on which the reference marks 14 are not displayed.

The reference point sensors 110 may include a plurality of sensing elements so as to detect signals detected from each of the at least two reference marks 14. Moreover, arrangement positions of the reference point sensors 110 may correspond to the display position of the at least two reference marks 14. The reference point sensors 110 may detect the signals detected from the at least two reference marks 14. Detecting methods of the signals detected from the reference marks 14 may vary. For example, the reference marks 14 may independently generate electrical signals or light signals and the reference point sensors 110 may detect the generated signals. As another example, when the reference marks 14 have constituents different from that of the surface of the subject 10, the reference point sensors 110 may measure signals that are the light signals or the electrical signals applied to and returned from the surface of the subject 10 on which the reference marks 14 are displayed. The reference point sensors 110 may distinguish the signals detected from the reference marks 14 from the signals detected from another portion of the reference marks 14 on which the reference marks 14 are not displayed.

Figure 3:
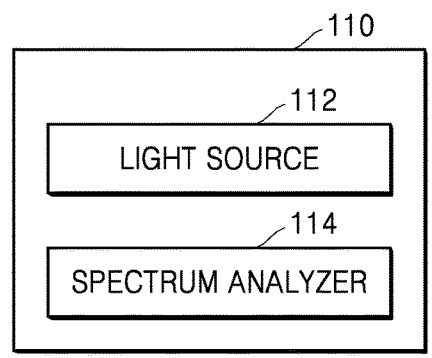
FIG. 3 is a block diagram of an example of detection sensors of FIGS. 1 and 2.

FIG. 3 is a block diagram of an example of sensors of FIGS. 1 and 2.

Referring to FIG. 3, the reference point sensors 110 may include a light source 112 to radiate light onto a surface of the subject 10 on which the reference marks 14 are displayed, and a spectrum analyzer 114 analyzing a spectrum of the light reflected from the reference marks 14. As described above, when the reference marks 14 have constituents different from that of the surface of the subject 10, the light reflected from the reference marks 14 and the light reflected from the another portion of the subject 10 on which the reference marks 14 are not displayed may have different spectrums. The spectrum analyzer 114 may analyze a spectrum of the light reflected from the subject 10 on which the reference marks 14 are displayed. The spectrum analyzer 114 may analyze an intensity distribution of each wavelength of the reflected lights. Furthermore, the spectrum information of the reflected lights may be provided to the biological signal measuring position detector 120.

Figure 4:
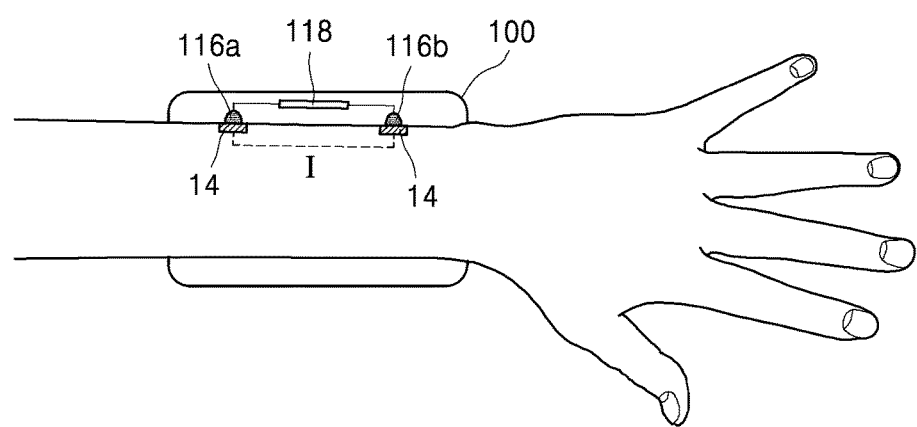
FIG. 4 is a view illustrating another example of the detection sensors of FIGS. 1 and 2.

FIG. 4 is a view illustrating another example of the sensors of FIGS. 1 and 2.

Referring to FIG. 4, the reference point sensors 110 may include at least two electrodes 116a and 116b to be in contact with a surface of the subject on which the reference marks are attached. The sensors 100 may also include an impedance measurer 118 measuring an impedance between the at least two electrodes 116a and 116b. The at least two electrodes 116a and 116b may correspond to the at least two reference marks 14. Therefore, an arrangement position of the electrodes 116a and 116b in the biological signal measuring apparatus 100 may also correspond to those of the reference marks 14 in the subject 10. FIG. 4 illustrates the electrodes 116a and 116b, and the impedance measurer 118 measuring the impedance between the two electrodes 116a and 116b but the exemplary embodiment is not limited thereto. For example, the reference point sensors 110 may include at least three electrodes and the impedance measurer 118 may measure an impedance between any two electrodes from among the electrodes.

As described above, when the constituent of the subject 10 is different from those of the reference marks 14, a constituent of a path I in which current flows between the electrodes 116a and 116b may change according to whether or not the electrodes 116a and 116b are disposed on the reference marks 14. In other words, the impedance between the electrodes 116a and 116b may change according to whether or not the electrodes 116a and 116b are disposed on the reference marks 14. The impedance measurer 118 may input a predetermined current through the electrodes 116a and 116b and measure a voltage between the electrodes 116a and 116b, and thus may measure the impedance between the electrodes 116a and 116b. As another example, the impedance measurer 118 may apply a predetermined voltage between the electrodes 116a and 116b and measure a current flowing between the electrodes 116a and 116b, and thus also may measure the impedance between the electrodes 116a and 116b. The impedance information measured by the impedance measurer 118 may be transmitted to the biological signal measuring position detector 120 that will be described below.

Referring again to FIG. 2, the biological signal measuring position detector 120 may receive information measured by the reference point sensors 110 and output the information about a biological signal measuring position. The information about the biological signal measuring position may include information about whether the biological signal measuring position matches the target measuring position 12. In addition, the information about the biological signal measuring position, if the biological signal measuring position is different from the target measuring position 12, may include information about whether a distance difference between them is within an allowable range. The allowable range may have a value corresponding to a reliability of the measured biological signal. For example, the allowable range may be set relatively large if the change in the reliability of the measured biological signal according to the position of the biological signal measured near the target measuring position 12 is relatively small. As another example, the allowable range may be set relatively small if the change in the reliability of the measured biological signal according to the position of the biological signal measured near the target measuring position 12 is relatively large.

In order to output the information about the biological signal measuring position, the biological signal measuring position detector 120 may store information about reference signals detected from the at least two reference marks 14. The reference signals may be signals detected from the reference marks 14 measured by the reference point sensors 110 when positions of the reference point sensors 110 match those of the reference marks 14. The information about the reference signals may be stored in advance in the biological signal measuring position detector 120 in a manufacturing process of the biological signal measuring apparatus 100. For example, a manufacturer of the biological signal measuring apparatus 100 may match positions of the reference point sensors 110 with those of the reference marks 14 and store signals detected from the reference marks 14 measured by the reference point sensors 110 as reference signals. As another example, a user may directly match positions of the reference point sensors 110 with those of the reference marks 14 and thus store and set signals measured by the reference point sensors 110 as reference signals.

When a difference between the signals detected from the reference marks 14 measured by the reference point sensors 110 and the reference signals is smaller than an allowable error, the biological signal measuring position may correspond to the target measuring position 12. That the biological signal measuring position corresponds to the target measuring position 12 may represent that the distance difference between the biological signal measuring position and the target measuring position 12 is within the allowable range.

The biological signal measuring position detector 120 may output the information about the biological signal measuring position by comparing the signals detected from the reference marks 14 with the reference signals. For example, the biological signal measuring position detector 120 may determine whether a ratio of the signals detected from the reference marks 14 and the reference signals is within an allowable error range in order to analyze the difference between the signals detected from the reference marks 14 and the reference signals. The biological signal measuring apparatus 100 may determine whether the distance difference between the biological signal measuring position and the target measuring position 12 is within the allowable error range. The analyzing method for comparing the signals detected from the reference marks 14 with the reference signals is not limited thereto. For example, the biological signal measuring position detector 120 may calculate the difference between the signals detected from the reference marks 14 and the reference signals, and may output information about the biological signal measuring position on the basis of the difference.

According to the type of the reference point sensors 110, an output method of the information about the biological signal measuring position of the biological signal measuring position detector 120 may also change. For example, the reference marks 14 may independently generate light signals or electrical signals. When positions of the reference point sensors 110 match those of the reference marks 14, the biological signal measuring position detector 120 may store information about the light signals or the electrical signals measured by the reference point sensors 110 as information about the reference signals. The reference signals may be stored in advance in the manufacturing process of the biological signal measuring apparatus 100 as described above, or a user may store a value measured at an initial measuring position as the reference signals. The biological signal measuring position detector 120 may compare the light signals or the electrical signals measured by the reference point sensors 110 with the reference signals. Furthermore, the biological signal measuring position detector 120 may determine whether the ratio of the light signals or the electrical signals measured by the reference point sensors 110 to the reference signals is within the allowable error range.

As another example, the reference marks 14 may have constituents different from that of the subject 10, and the reference point sensors 110 may include at least two electrodes 116a and 116b and the impedance measurer 118 as illustrated in FIG. 4. The biological signal measuring position detector 120 may store an impedance value measured by the impedance measurer 118 as information about the reference signals when positions of the electrodes 116a and 116b of the reference point sensors 110 match those of the reference marks 14. The reference signals may be stored in advance in the manufacturing process of the biological signal measuring apparatus 100 as described above, or a user may store a value measured at an initial measuring position as the reference signals. The biological signal measuring position detector 120 may compare an impedance value measured by the impedance measurer 118 with an impedance value with respect to the reference signals. For example, the biological signal measuring position detector 120 may determine whether the ratio of the impedance value measured by the impedance measurer 118 to the impedance value with respect to the reference signals is within an allowable range.

As further another example, the reference marks 14 may have material different from that of the subject 10, and the reference point sensors 110 may include the light source 112 and the spectrum analyzer 114 as illustrated in FIG. 3. In this case, the biological signal measuring position detector 120 may store a spectrum of the light measured by the reference point sensors 110 as information about the reference signals when positions of the reference point sensors 110 match those of the reference marks 14. The reference signals may be stored in advance in the manufacturing process of the biological signal measuring apparatus 100 as described above, or a user may store a value measured at an initial measuring position as the reference signals. Since constituents of the reference marks 14 is different from that of the surface of the subject 10, a spectrum curve of the light measured by the reference point sensors 110 may change according to whether the positions of the reference point sensors 110 match those of the reference marks 14.

Figure 5:
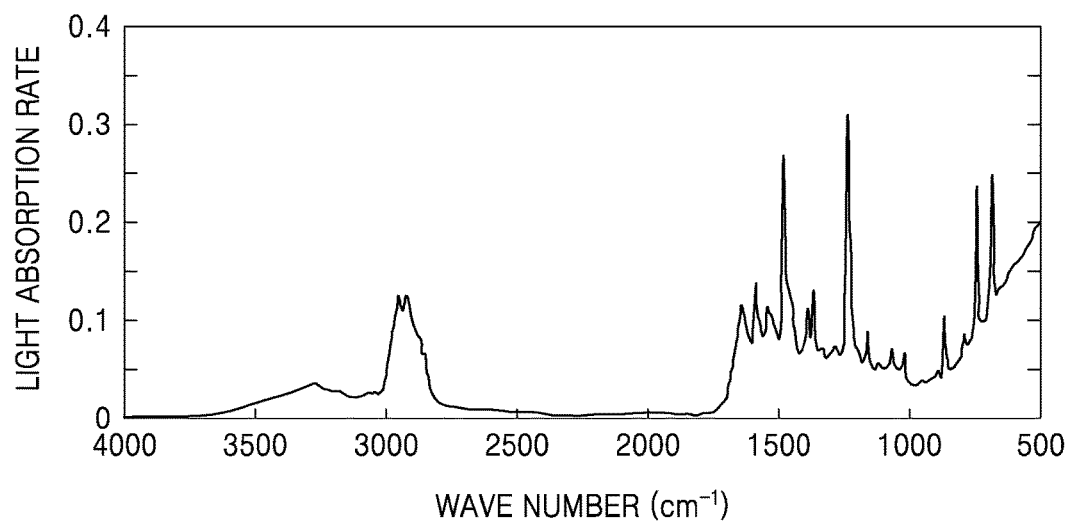
FIG. 5 is a graph illustrating an example of a result of an absorption spectrum measured from light reflected from the skin of a human body on which light is radiated.

FIG. 5 is a graph illustrating an example of a result of an absorption spectrum measured from light reflected from the skin of a human body on which light is radiated.

In FIG. 5, a vertical axis represents a light absorption rate and a horizontal axis represents a wave number of the light. As shown in FIG. 5, spectrum peaks are formed near about 3000 cm$^{-1}$, 1000 cm$^{-1}$ to 1500 cm$^{-1}$, and 600 cm$^{-1}$ of the wave number. This is because that moisture included in the skin efficiently absorbs light having a wave number of about 3000 cm$^{-1}$, protein efficiently absorbs light having a wave number of about 1000 cm$^{-1}$ to 1500 cm$^{-1}$, and amid II efficiently absorbs light having a wave number of about 600 cm$^{-1}$.

Figure 6:
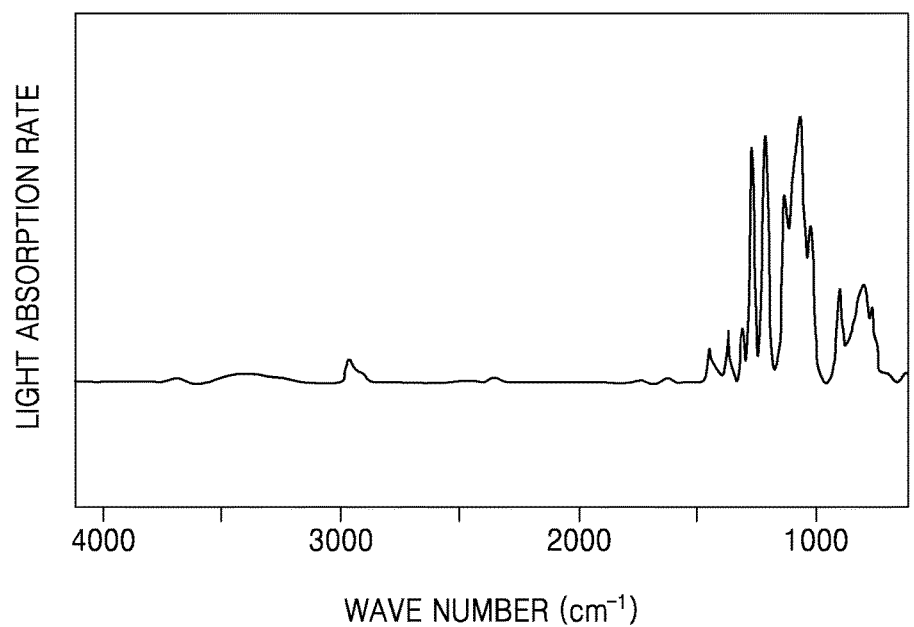
FIG. 6 is a graph illustrating an example of a result of an absorption spectrum measured from light reflected from polydimethylsiloxane (PDMS), which is an example of a material which may be included in reference marks when light is radiated onto the polydimethylsiloxane (PDMS)

FIG. 6 is a graph illustrating an example of a result of an absorption spectrum measured from light reflected from polydimethylsiloxane (PDMS), which is an example of material which may be included in the reference marks 14.

In FIG. 6, a vertical axis represents a light absorption rate and a horizontal axis represents a wave number of the light. As shown in FIG. 6, a plurality of spectrum peaks are formed within the range of about 900 cm$^{-1}$ to 1300 cm$^{-1}$ of the wave number. For example, spectrum peaks may be formed near about 903 cm$^{-1}$, 1064 cm$^{-1}$, and 1267 cm$^{-1}$ of the wave number. That is, PDMS may have a high light absorption rate in a wave number region different from skin. Therefore, when the subject 10 is a human body and the reference marks include PDMS material, a spectrum curve obtained from the spectrum analyzer 114 may more resemble the spectrum curve of FIG. 6 rather than the spectrum curve of FIG. 5 as the position of the reference point sensors 110 becomes closer to the reference marks 14. In other words, the spectrum peaks of FIG. 6 are gradually higher as the position of the reference point sensors 110 becomes closer to the reference marks 14 while the spectrum peaks of FIG. 5 are gradually lowered.

The biological signal measuring position detector 120 may store a spectrum of the light measured by the spectrum analyzer 114 as information about the reference signals when positions of the reference point sensors 110 match those of the reference marks 14. The reference signals may be stored in advance in the manufacturing process of the biological signal measuring apparatus 100 as described above, or a user may store a value measured at an initial measuring position as the reference signals. The biological signal measuring position detector 120 may compare the spectrum of the light measured by the spectrum analyzer 114 with a spectrum of the light with respect to the reference signals. For example, the biological signal measuring position detector 120 may determine whether a ratio of a peak value in the range of a predetermined wavelength shown in a spectrum analyzed by the spectrum analyzer 114 to a peak value in the range of a predetermined wavelength shown in a spectrum with respect to the reference signals is within an allowable error range.

Figure 7A:
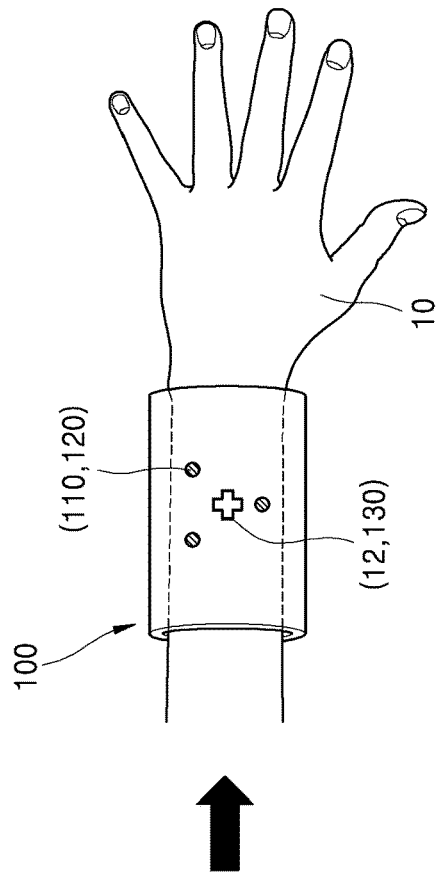
FIG. 7A is a view illustrating a case where a biological signal measuring position does not coincide with the target measuring position.
Figure 7B:
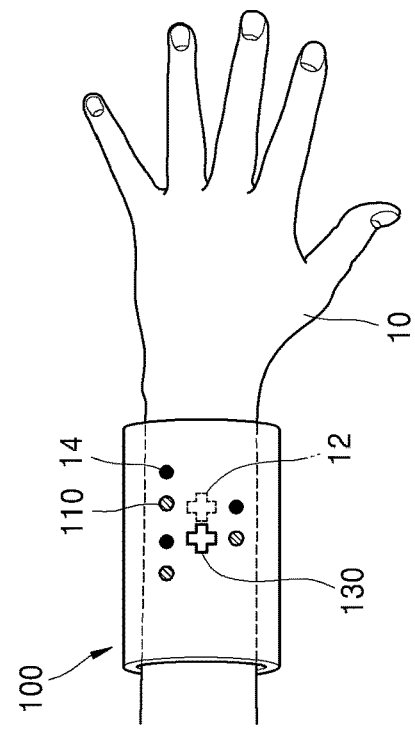
FIG. 7B is a view illustrating a case where the biological signal measuring position coincides with the target measuring position.

FIG. 7A is a view illustrating a case where a biological signal measuring position does not coincide with the target measuring position, and FIG. 7B is a view illustrating a case where a biological signal measuring position coincides with the target measuring position. An operating method of the biological signal measuring sensor 130 may change in FIGS. 7A and 7B.

FIG. 7A shows that a position of the biological signal measuring sensor 130 is deviated from the target measuring position 12 as a position of the reference point sensors 110 becomes deviated from the reference marks 14. In the case of FIG. 7A, the biological signal measuring position detector 120 may determine that a ratio of signals detected from the reference marks to the reference signals is not within an allowable error range. Therefore, the biological signal measuring sensor 130 may interrupt biological signal measuring on the basis of a determination result of the biological signal measuring position detector 120. This is due to reduction in reliability of the measured data. As another example, in the case of FIG. 7A, the biological signal measuring sensor 130 may determine that the measured biological signal data is invalid data and thus not store or separately manage the measured biological signal data.

FIG. 7B shows an adjusted position of the biological signal measuring apparatus 100. information about the biological signal measuring position that is outputted from the biological signal measuring position detector 120 may be changed when the position of the biological signal measuring apparatus 100 is adjusted as above. In other words, the biological signal measuring position detector 120 may determine that the biological signal measuring position corresponds to the target measuring position 12 when the position of the reference point sensors 110 is adjusted so as to be matched with the reference marks 14. Therefore, the biological signal measuring sensor 130 may continue the biological signal measuring on the basis of determination of the biological signal measuring position detector 120 as the reliability of the measured data is maintained.

Figure 8:
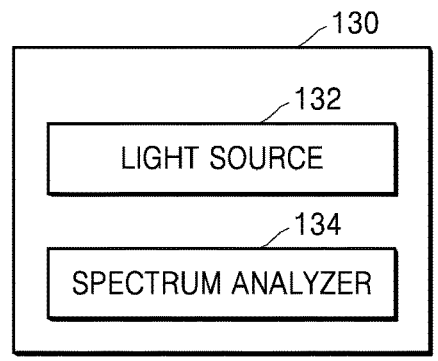
FIG. 8 is a block diagram of a biological signal measuring sensor according to an embodiment.
Figure 9:
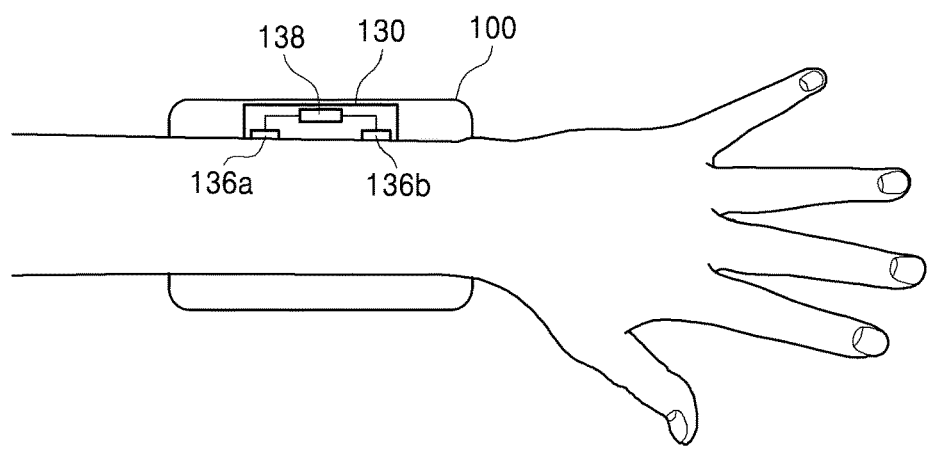
FIG. 9 is a view illustrating the biological signal measuring sensor according to another exemplary embodiment.

The biological signal measuring sensor 130 may measure a biological signal of the subject 10 in various manners. FIG. 8 is a block diagram of a biological signal measuring sensor according to an exemplary embodiment. FIG. 9 is a view illustrating the biological signal measuring sensor according to another exemplary embodiment.

Referring to FIG. 8, the biological signal measuring sensor 130 may include a light source 132 to radiate light to a biological signal measuring position and a spectrum analyzer 134 analyzing a spectrum of the light reflected from the biological signal measuring position. In this case, the biological signal measuring sensor 130 may provide information about a constituent distributed in a surface of the subject 10 from the spectrum of the light obtained from the spectrum analyzer 134.

Referring to FIG. 9, the biological signal measuring sensor 130 may include at least two electrodes 136a and 136b formed in the biological signal measuring position and an impedance measurer 138 measuring an impedance between at least two electrodes 136a and 136b. In this case, the biological signal measuring sensor 130 may provide information about a constituent forming the subject 10 or a blood vessel size of the subject 10 from the impedance information measured by the impedance measurer 138.

FIGS. 1 and 2 illustrate that the reference point sensors 110 and the biological signal measuring sensor 130 are physically separated from each other, but the configuration is not limited thereto. For example, the reference point sensors 110 and the biological signal measuring sensor 130 may be supplied with power from an identical power source. The reference point sensors 110 and the biological signal measuring sensor 130 may detect light radiated from the identical power source independently from each other and may respectively use the light for signal measuring.

Figure 10:
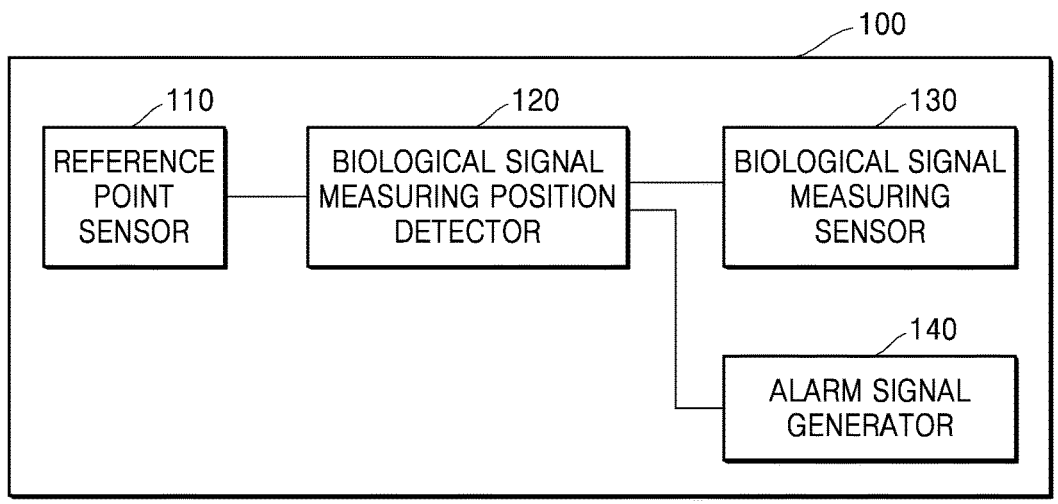
FIG. 10 is a block diagram of a modified example of the biological signal measuring apparatus of FIG. 2.

FIG. 10 is a block diagram of a modified example of the biological signal measuring apparatus 100 of FIG. 1.

Referring to FIG. 10, the biological signal measuring apparatus 100 may include an alarm signal generator 140 to generate an alarm signal when the biological signal measuring position detector 120 determines that a ratio of signals detected from the reference marks 14 and the reference signals is not within an allowable error range. The alarm signal generator 140 may be formed in various manners. For example, the alarm signal generator 140 may include a display or a bulb visually showing the alarm signal. As another example, the alarm signal generator 140 may include a speaker that generates the alarm signal as an alarm sound to be heard.

The biological signal measuring apparatus 100 according to an exemplary embodiment is described above by referring to FIGS. 1 to 10. A biological signal measuring method using the biological signal measuring apparatus 100 according to another exemplary embodiment will be described below. The embodiments of the biological signal measuring apparatus 100 described above may be applied to the biological signal measuring method described below.

Figure 11:
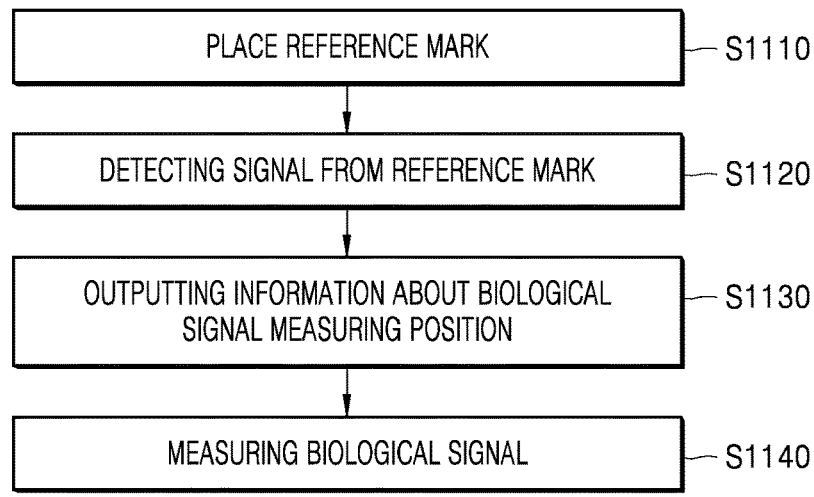
FIG. 11 is a flow chart illustrating a biological signal measuring method according to an exemplary embodiment.

FIG. 11 is a flow chart illustrating a biological signal measuring method according to an exemplary embodiment.

Referring to FIG. 11, the biological signal measuring method according to the exemplary embodiment may include detecting signals detected from at least two reference marks 14 attached on a surface of the subject 10 (S1120), outputting information about a biological signal measuring position based on the signals detected from the at least two reference marks 14 (S1130), and measuring the biological signal according to the information about the biological signal measuring position (S1140).

In addition, the biological signal measuring method may include placing the reference marks on the surface of the subject 10 (S1110) in order to perform the operation (S1120) of detecting signals detected from the at least two reference marks 14. The reference marks may be placed or attached by using at least one of a tattoo sticker, an adhesive tape, or an E-skin on which the at least two reference marks are attached, but is not limited thereto.

The operation (S1120) of detecting signals detected from the marks and the step (S1140) of measuring the biological signal may use the method of radiating the light and analyzing the spectrum, and the method of measuring the impedance between the two electrodes, as described above by referring to FIGS. 3 and 4, but are not limited thereto.

Figure 12:
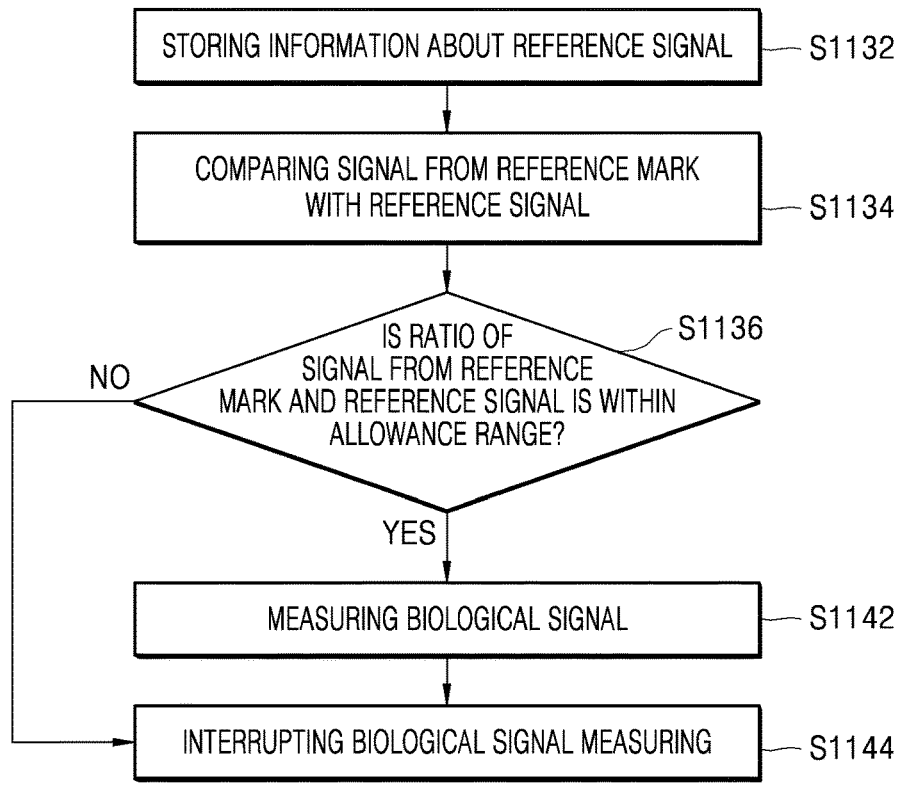
FIG. 12 is a flow chart illustrating an example of an operating method of outputting information about a biological signal measuring position and measuring a biological signal.

FIG. 12 is a flow chart illustrating an example of an operating method of the operation (S1130) of outputting information about a biological signal measuring position and the o (S1140) of measuring the biological signal.

Referring to FIG. 12, the operation (S1130) of outputting information about the biological signal measuring position may include storing information about reference signals corresponding to the at least two reference marks 14 (S1132), comparing the signals detected from the reference marks 14 with the reference signals (S1134), and determining whether a ratio of the signals detected from the reference marks 14 to the reference signals is within an allowable range (S1136). Furthermore, the operation (S1140) of measuring the biological signal may include measuring a biological signal when the ratio of the signals detected from the reference marks 14 to the reference signals is within the allowable range (S1142), and interrupting the biological signal measuring when the ratio of the signals detected from the reference marks 14 to the reference signals is beyond the allowable range (S1144).

Figure 13:
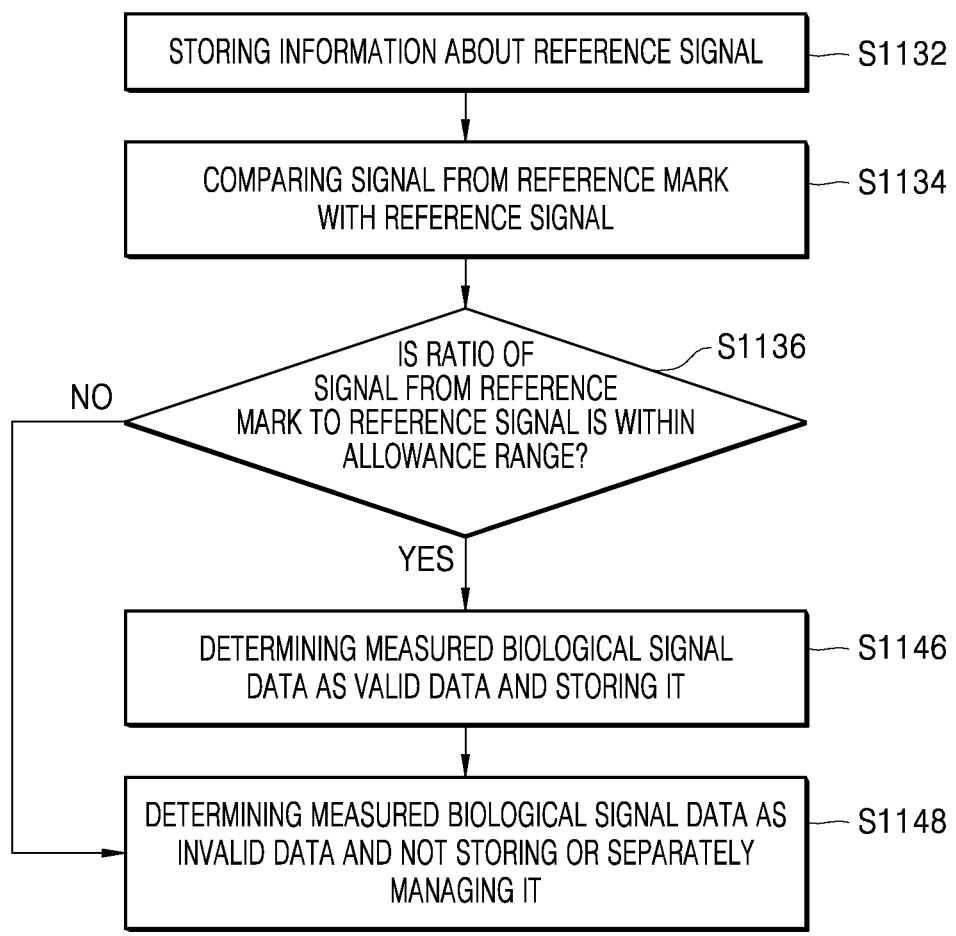
FIG. 13 is a flow chart illustrating another example of the operating method of outputting information about the biological signal measuring position and measuring of the biological signal.

FIG. 13 is a flow chart illustrating another example of the operating method of the operation (S1130) of outputting information about a biological signal measuring position and the operation (S1140) of measuring the biological signal.

Referring to FIG. 13, the operation (S1130) of outputting information about the biological signal measuring position may include storing information about reference signals corresponding to the at least two reference marks 14 (S1132_, comparing the signals detected from the reference marks 14 with the reference signals (S1134), and determining whether a ratio of the signals detected from the reference marks 14 to the reference signals is within an allowable range (S1136). Furthermore, the operation (S1140) of measuring the biological signal may include determining the measured biological signal data as valid data and storing it when the ratio of the signals detected from the reference marks 14 to the reference signals is within the allowable range (S1146), and determining that the measured biological signal data is invalid data and thus not storing or separately managing the measured biological signal data when the ratio of the signals detected from the reference marks 14 and the reference signals is beyond the allowable range (S1148).

Figure 14:
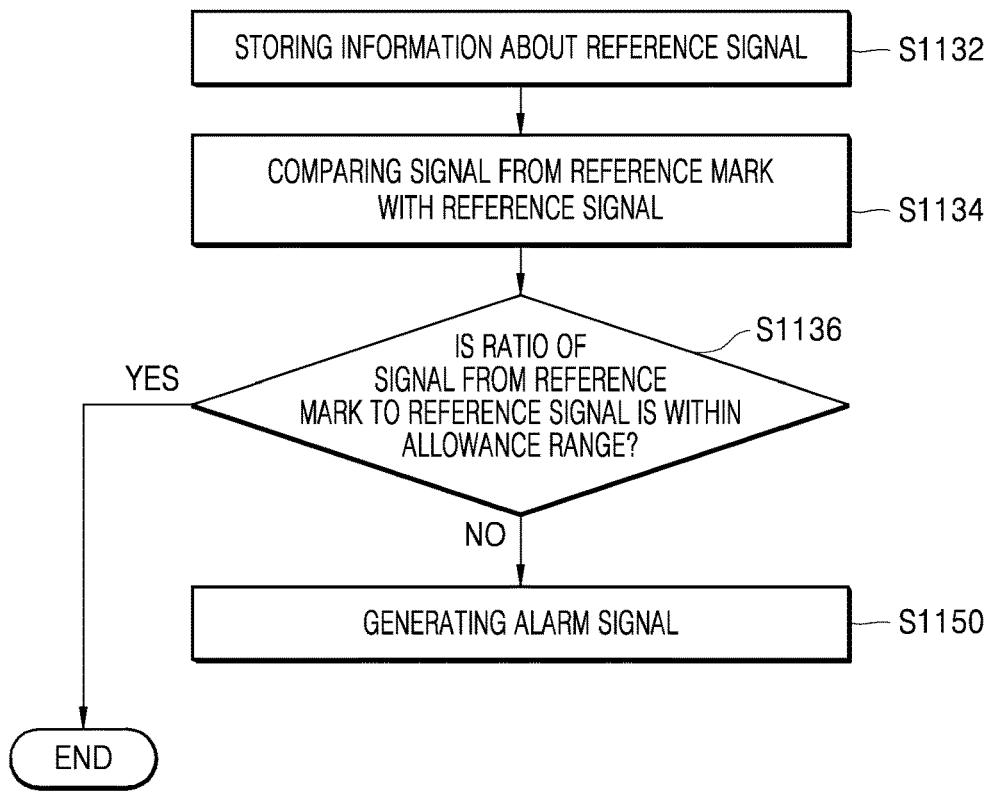
FIG. 14 is a flow chart illustrating a biological signal measuring method including generating of an alarm signal, according to an exemplary embodiment.

According to the biological signal measuring method of the exemplary embodiment, the alarm signal may be generated when the biological signal measuring position is deviated from the target measuring position 12. FIG. 14 is a flow chart illustrating a biological signal measuring method including generating of an alarm signal, according to an exemplary embodiment.

Referring to FIG. 14, the biological signal measuring method may include generating the alarm signal (S1150) when it is determined that the ratio of the signals detected from the reference marks 14 to the reference signals is outside the allowable range in operation S1136 operation. The operation (S1150) of generating the alarm signal may generate the alarm signal visually through a display or a bulb, or may generate audibly through a speaker.

The biological signal measuring apparatus 100 and the method thereof according to the exemplary embodiments has been described above referring to FIGS. 1 to 10. A biological signal measuring apparatus and a method thereof according to another exemplary embodiment will be described below.

Figure 15:
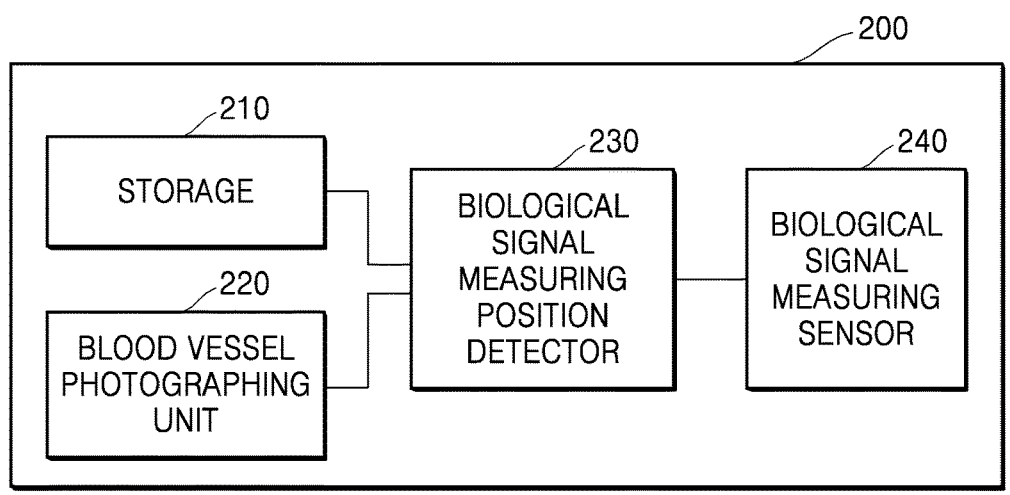
FIG. 15 is a block diagram illustrating a biological signal measuring apparatus according to another exemplary embodiment.

FIG. 15 is a block diagram illustrating a biological signal measuring apparatus 200 according to another exemplary embodiment.

Referring to FIG. 15, the biological signal measuring apparatus 200 according to the exemplary embodiment may include a storage 210 to store a reference blood vessel image photographed at a reference point on a subject, and a blood vessel photographing unit 220 to photograph a blood vessel image of the subject. The reference point (also referred to as "reference area") may be a point or area of the subject at which the biological signal is measured. Furthermore, the biological signal measuring apparatus 200 may include a biological signal measuring position detector 230 to output information about a biological signal measuring position by comparing the blood vessel image photographed at the blood vessel photographing unit 220 and the reference blood vessel image, and a biological signal measuring sensor 240 to measure the biological signal based on the information about the biological signal measuring position.

Figure 16:
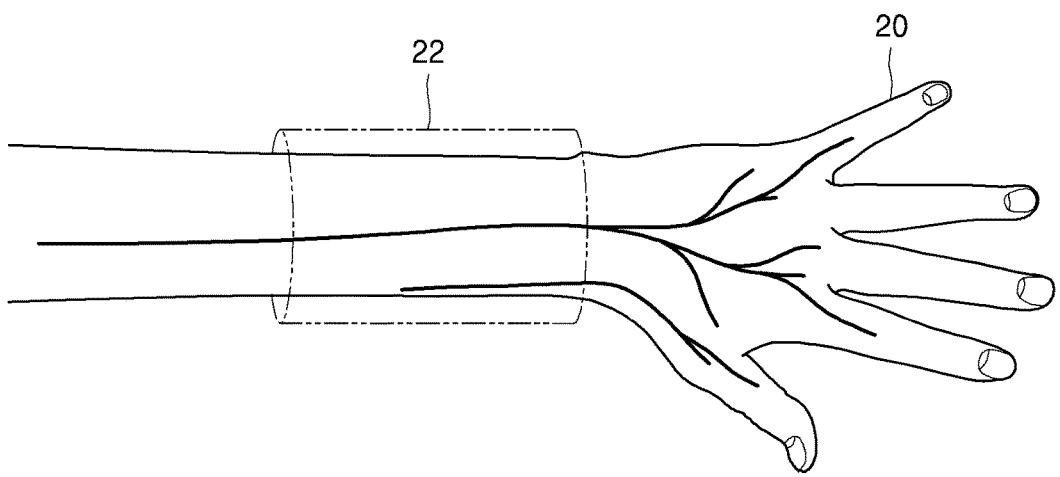
FIG. 16 is a view illustrating a blood vessel image at and near a reference point on a subject.

FIG. 16 is a view illustrating a blood vessel image shown at and near a reference point 22 set in a subject 20.

The subject 20 is a human body and the reference area 22 is an arm of the human body in FIG. 16. However, this is only an example, the subject type and the reference area or point may change as needed. Referring to FIG. 16, blood vessels are distributed in the arm and a hand of the subject 20. The blood vessel image may change corresponding to the subject 20 and the position of the subject 20. Therefore, it is possible to obtain not only information about the subject 20 itself but also information about the area at which the blood vessel image is photographed by photographing the blood vessel image.

Figure 17:
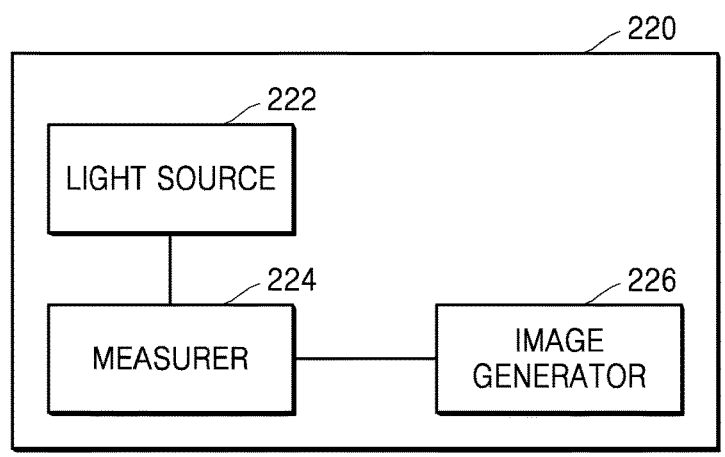
FIG. 17 is a block diagram of an example of a blood vessel photographing unit.

The blood vessel photographing unit 220 may photograph the blood vessel image of the subject 20 in various manners. FIG. 17 is a block diagram of an example of the blood vessel photographing unit 220.

Referring to FIG. 17, the blood vessel photographing unit 220 may include a light source 222 that may radiate light onto a surface of the subject, a measurer 224 that may measure a light absorption rate with respect to the subject 20, and an image generator 226 that may generate the blood vessel image based on the infrared absorption rate measured by the measurer 224. Since blood has an infrared absorption rate different from that of another tissue of the subject 20, the blood vessel image may be generated by measuring the infrared absorption rate in the subject 20.

The light source 222 may radiate lights having wavelengths that may be better or not absorbed by blood than other tissues of the subject 20. For example, the light source 222 may radiate light of a wavelength band of about 850 nm to 980 nm, which has a high blood absorption rate with respect to hemoglobin. As another example, the light source 222 may radiate light of a wavelength band of about 390 nm to 750 nm, which has a low blood absorption rate with respect to hemoglobin.

The measurer 224 may sense a signal of a reflected light or a transmitted light from the subject 20. The image generator 226 may generate the blood vessel image from measured data of the measurer 224. The image generator 226 may generate blood vessel coordinate data from absorption rate data measured by the measurer 224. The blood vessel coordinate data may include information about depth at which blood vessel is located and thickness of the blood vessel in the subject 20.

It can be known whether a biological signal measuring position matches with the reference point 22 by comparing the blood vessel image photographed at the reference point 22 to measure a biological signal with the blood vessel image photographed at the biological signal measuring position to measure the biological signal in the subject 20. Therefore, the biological signal measuring position detector 230 may compare a blood vessel image photographed by the blood vessel photographing unit 220 with the reference blood vessel image stored in the storage 210. The biological signal measuring position detector 230 may determine whether a similarity of the blood vessel image photographed by the blood vessel photographing unit 220 and the reference blood vessel image is within an allowable range. The similarity may be determined by information about whether the blood vessels shown in the two images are overlapped in a predetermined ratio or more and a distance needs to be shifted in order to overlap the two images.

An operating method of the biological signal measuring sensor 240 may change according to whether information about the biological signal measuring position outputted from the biological signal measuring position detector 230 matches with the reference point 22. For example, the biological signal measuring sensor 240 may measure the biological signal when the similarity is within an allowable range, and may interrupt the biological signal measuring when the similarity is outside the allowable range. As another example, the biological signal measuring sensor 240 may store the measured data as valid data when the similarity is within the allowable range, or may determine the measured biological signal data as invalid data and thus not store or separately manage it when the similarity is beyond the allowable range.

The embodiments described referring to FIGS. 8 and 9 of may be applied to the biological signal measuring sensor 240. Therefore, the biological signal measuring sensor 240 may include the light source and the spectrum analyzer. Furthermore, the biological signal measuring sensor 240 may include at least two electrodes and the impedance measurer to measure an impedance between the at least two electrodes.

Figure 18:
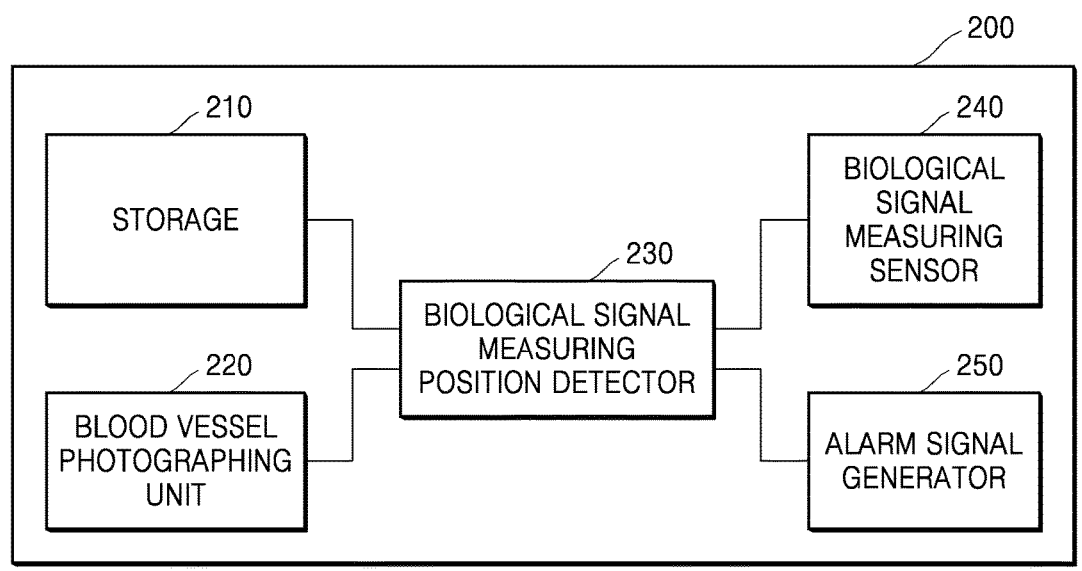
FIG. 18 is a block diagram illustrating a biological signal measuring apparatus 200 according to an exemplary embodiment.

The biological signal measuring apparatus 200 may generate an alarm signal when the biological signal measuring position is deviated from the reference point 22. FIG. 18 is a block diagram of the biological signal measuring apparatus 200 according to an exemplary embodiment.

Referring to FIG. 18, biological signal measuring apparatus 200 may include an alarm signal generator 250. The alarm signal generator 250 may generate an alarm signal if the biological signal measuring position detector 230 determines that a similarity of the blood vessel image photographed by the blood vessel photographing unit 220 and the reference blood vessel image is not within an allowable range. The alarm signal generator 250 may include a display or a bulb to visually generate the alarm signal. As another example, the alarm signal generator 250 may include a speaker to audibly generate the alarm signal.

The biological signal measuring apparatus 200 according to an exemplary embodiment is described above by referring to FIGS. 15 to 18. A biological signal measuring method using the biological signal measuring apparatus 200 according to another exemplary embodiment will be described below. The whole embodiments described above by referring to FIGS. 15 to 18 may be applied to the biological signal measuring method described below.

Figure 19:
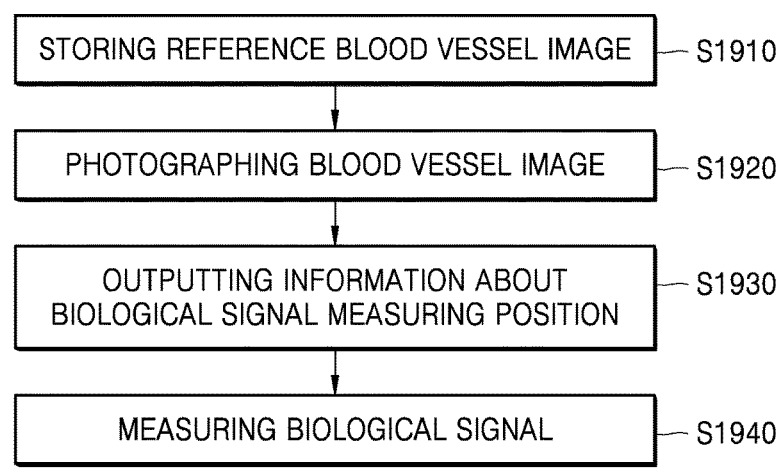
FIG. 19 is a flow chart illustrating a biological signal measuring method according to another exemplary embodiment.

FIG. 19 is a flow chart illustrating a biological signal measuring method according to another exemplary embodiment.

Referring to FIG. 19, the biological signal measuring method according to the exemplary embodiment may include storing a reference blood vessel image photographed at the reference point 22 of the subject 20 (S1910), photographing a blood vessel image of the subject 20 (S1920), comparing the blood vessel image photographed at the operation S1920 with the reference blood vessel image and outputting information about a biological signal measuring position (S1930), and measuring a biological signal based on the information about the biological signal measuring position (S1940).

The operation (S1920) of photographing the blood vessel image may radiate light onto the subject 20, measure a light absorption rate and generate the blood vessel image by using the light absorption rate. However, this is only a sample, the biological signal measuring method is not limited thereto. Furthermore, the operation (S1930) of outputting information about the biological signal measuring position may include analyzing whether a similarity of the blood vessel image photographed and the reference blood vessel image is within an allowable range. In addition, operation S1940 may include measuring the biological signal only when the similarity is within the allowable range. As another example, operation S1940 may include measuring the measured data as valid data when the similarity is within the allowable range, or may determine the measured biological signal data as invalid data and thus not store or separately manage it when the similarity is beyond the allowable range.

Figure 20:
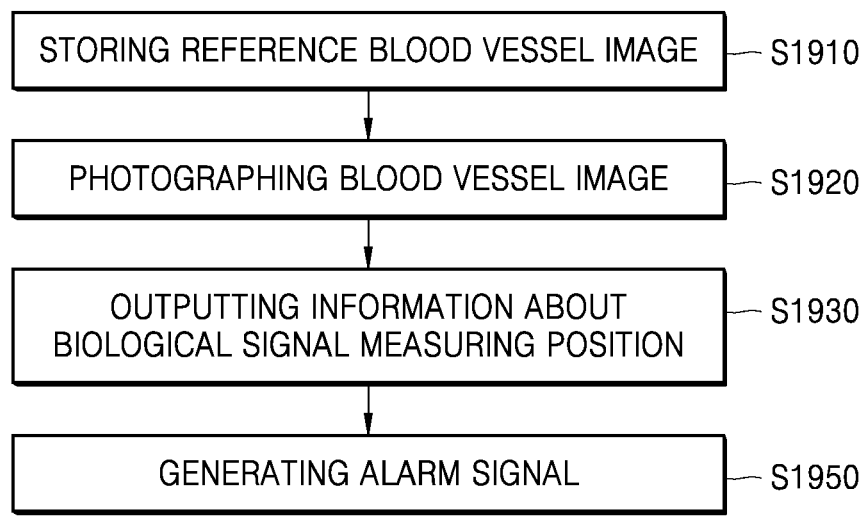
FIG. 20 is a flow chart illustrating a modified example of the biological signal measuring method of FIG. 19.

FIG. 20 is a flow chart illustrating a modified example of the biological signal measuring method of FIG. 19.

Referring to FIG. 20, the biological signal measuring method according to the exemplary embodiment may include storing a reference blood vessel image photographed at a reference point 22 of the subject 20 (S1910), photographing a blood vessel image of the subject 20 (S1920), comparing the blood vessel image photographed at operation S1920 with the reference blood vessel image and outputting information about the biological signal measuring position (S1930), and generating an alarm signal when the biological signal measuring position is deviated from the reference point 22 (S1950).

The biological signal measuring apparatuses 100 and 200 and the method thereof according to the exemplary embodiments are described above by referring to FIGS. 1 to 20. According to the embodiments, a reliability of the measured biological signal data may be improved by uniformly maintain the biological signal measuring position at which the biological signal measuring apparatuses 100 and 200 measure the biological signal.

The biological signal measuring apparatuses 100 and 200 and the method thereof according to the exemplary embodiments described above may be applied to various devices such as a mobile or a wearable apparatus to provide a health care function.

As described above, according to the one or more of the above exemplary embodiments, reliability of measured biological signal data may be improved by uniformly maintain a biological signal measuring position.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art

What is claimed is:

1. A biological signal measuring apparatus comprising:
at least two reference marks configured to generate a light signal or an electrical signal;
a plurality of reference point sensors configured to detect signals from at least two reference points indicated by the at least two reference marks on a surface of a subject;
a biological signal measuring position detector configured to:
pre-store information about reference signals detected from the at least two reference marks based on positions of the plurality of reference point sensors matching those of the at least two reference marks,
compare the signals detected from the at least two reference points with the reference signals, and
in response to a degree of similarity between the signals detected from the at least two reference points and the reference signals being within an allowable range, generate information about a biological signal measuring position indicating that the biological signal measuring position corresponds to a target position; and
a biological signal measuring sensor configured to obtain a biological signal with respect to the target position on the surface of the subject based on the information about the biological signal measuring position,
wherein the allowable range has a value that is determined based on a change in a reliability of the biological signal according to a distance from the target position.

2. The biological signal measuring apparatus of claim 1, wherein the biological signal measuring sensor is further configured to start obtaining the biological signal in response to generation of the information about the biological signal measuring position.

3. The biological signal measuring apparatus of claim 1, wherein the biological signal measuring sensor is further configured to start determining and storing the obtained biological signal as a valid signal in response to generation of the information about the biological signal measuring position.

4. The biological signal measuring apparatus of claim 1, wherein each of the plurality of reference point sensors comprises a light source configured to radiate a light onto the surface of the subject at the at least two reference points on which the at least two reference marks are disposed and a spectrum analyzer configured to analyze a spectrum of the light reflected from the surface of the subject.

5. The biological signal measuring apparatus of claim 1, wherein each of the plurality of reference point sensors comprises at least two electrodes that are in contact with the surface of the subject at the at least two reference points on which the at least two reference marks are disposed and an impedance measurer configured to obtain an impedance between the at least two electrodes.

6. The biological signal measuring apparatus of claim 1, wherein the biological signal measuring sensor comprises a light source configured to radiate a light onto the biological signal measuring position and a spectrum analyzer configured to analyze a spectrum of the light reflected from the biological signal measuring position.

7. The biological signal measuring apparatus of claim 1, wherein the biological signal measuring sensor comprises at least two electrodes placed at the biological signal measuring position and an impedance measurer configured to obtain an impedance between the at least two electrodes.

8. The biological signal measuring apparatus of claim 1, wherein the plurality of reference point sensors are configured to detect the signals from the at least two reference points indicated by the at least two reference marks on the surface of the subject, each of the at least two reference marks comprising at least one of polydimethylsiloxane (PDMS) and epoxy resin.

9. The biological signal measuring apparatus of claim 1, wherein the plurality of reference point sensors are configured to detect the signals from the at least two reference points indicated by the at least two reference marks on the surface of the subject, the at least two reference marks being disposed on the surface of the subject by using at least one of a tattoo sticker, an adhesive tape, and an E-skin.

10. The biological signal measuring apparatus of claim 1, further comprising:
an alarm signal generator configured to generate an alarm signal in response to the degree of similarity between the signals detected from the at least two reference points and the reference signals being not within the allowable range.

11. The biological signal measuring apparatus of claim 1, wherein the allowable range is determined to be relatively large based on the change in the reliability of the biological signal according to the distance from the target position being relatively small, and the allowable range is determined to be relatively small based on the change in the reliability of the biological signal according to the distance from the target position being relatively large.

12. A biological signal measuring method by a biological signal measuring apparatus comprising a plurality of reference point sensors, a biological signal measuring position detector, and a biological signal measuring sensor, the biological signal measuring method comprising:
pre-storing information about reference signals, the reference signals detected from at least two reference marks based on positions of the plurality of reference point sensors matching those of the at least two reference marks, the at least two reference marks configured to generate a light signal or an electrical signal;
detecting, by the plurality of reference point sensors, signals from at least two reference points indicated by the at least two reference marks on a surface of a subject;
comparing the signals detected from the at least two reference points with the reference signals;
in response to a degree of similarity between the signals detected from the at least two reference points and the reference signals being within an allowable range, generating information about a biological signal measuring position indicating that the biological signal measuring position corresponds to a target position; and
obtaining, by the biological signal measuring sensor, a biological signal with respect to the target position on the surface of the subject based on the information about the biological signal measuring position,
wherein the allowable range has a value that is determined based on a change in a reliability of the biological signal according to a distance from the target position.

13. The biological signal measuring method of claim 12, wherein the obtaining the biological signal is started in response to the generating the information about the biological signal measuring position.

14. The biological signal measuring method of claim 12, wherein the obtaining the biological signal comprises starting a process of determining and storing the obtained biological signal as a valid signal in response to the generating the information about the biological signal measuring position.

* * * * *